(12) United States Patent
Sarstedt

(10) Patent No.: US 6,672,345 B2
(45) Date of Patent: Jan. 6, 2004

(54) APPARATUS FOR FORMING A VACUUM IN A BLOOD TUBE

(75) Inventor: Walter Sarstedt, Numbrecht (DE)

(73) Assignee: Sarstedt AG, Numbrecht (DE)

( * ) Notice: Subject to any disclaimer, the term of this patent is extended or adjusted under 35 U.S.C. 154(b) by 0 days.

(21) Appl. No.: 10/263,339

(22) Filed: Oct. 2, 2002

(65) Prior Publication Data

US 2003/0069519 A1 Apr. 10, 2003

(30) Foreign Application Priority Data

Oct. 6, 2001 (DE) .......................... 101 49 435

(51) Int. Cl.⁷ .............................................. B65B 31/08
(52) U.S. Cl. ........................ 141/330; 141/65; 604/411
(58) Field of Search .................. 141/7, 8, 65, 329, 141/330; 600/577; 604/411

(56) References Cited

U.S. PATENT DOCUMENTS

| | | |
|---|---|---|
| 3,136,440 A | 6/1964 | Krug et al. |
| 4,036,387 A | 7/1977 | Feaster |
| 5,285,823 A * | 2/1994 | Honda ............................ 141/7 |
| 5,313,969 A * | 5/1994 | Hsieh ........................... 600/577 |

FOREIGN PATENT DOCUMENTS

DE 29 08 817 9/1990

* cited by examiner

*Primary Examiner*—Gregory L. Huson
*Assistant Examiner*—Peter deVore
(74) *Attorney, Agent, or Firm*—Herbert Dubno; Andrew Wilford

(57) ABSTRACT

A tube holding a sample of blood and having an end provided with a pierceable closure is partially evacuated of gas by an apparatus that has a stationary guide defining an axis inclined at an angle to the horizontal. A needle fixed in the guide projects axially downward therein. A slide in the guide forms a downwardly inclined and open seat centered on the axis and adapted to receive the end of the tube. The slide is movable in the guide between an outer position with the seat spaced past an end of the needle and an inner use position with the needle projecting into the seat so that in the use position the needle projects through the closure of the tube fitted to the seat. The slide is urged axially downward in the guide, and a pump is provided for aspirating air through the needle.

3 Claims, 2 Drawing Sheets

APPARATUS FOR FORMING A VACUUM IN A BLOOD TUBE

FIELD OF THE INVENTION

The present invention relates to a blood tube. More particularly this invention concerns an apparatus for forming a partial vacuum in a blood tube.

BACKGROUND OF THE INVENTION

As described in U.S. Pat. No. 3,136,440 of A. Krug a standard blood tube, in which a sample of a patient's blood is held after being drawn and before being subjected to whatever tests are required, is typically formed as a hard plastic or glass tubular vessel having a mouth sealed by an elastomeric membrane or plug. Such a blood tube is a disposable item that is mass produced.

When the tube is to be opened so that the blood can be tested, it is necessary to tear off the membrane or pull out the plug. This action typically creates a momentary superatmospheric pressure in the container so that any blood around the mouth can be expelled as an aerosol during the opening operation. Obviously this can be extremely dangerous for the person handling blood samples that may carry a deadly communicable disease.

It has been suggested to provide a special opening apparatus, but such machinery is complex, creates sterility problems in itself, and represents a bottleneck in the handling of blood samples in a laboratory. A system described in U.S. Pat. No. 4,036,387 of W. Feaster allows blood to be withdrawn from a filled sealed tube wholly by a device which protects the user, but this system is fairly complex and expensive.

Hence it has been suggested in German 2908817 of W. Feaster to depressurize, that is form a partial vacuum, in the tube after it is filled. In this manner, when the closure is removed, there will be a small flow of air into the tube, so that any drops of blood at the closure will not be expelled. Instead they will be sucked back in. In the system of DE 2908817 the blood-filled tube is oriented horizontally and a needle is pierced through its closure to suck out some of the air in the tube and produce the desired partial vacuum. Such a machine has the considerable problem that occasionally, particularly when the tube is quite full, that the air-aspirating needle can get contaminated. As a result infectious agents can be transferred from one sample to the next.

OBJECTS OF THE INVENTION

It is therefore an object of the present invention to provide an improved apparatus for forming a partial vacuum in a blood tube.

Another object is the provision of such an improved apparatus for forming a partial vacuum in a blood tube which overcomes the above-given disadvantages, that is which is simple and easy to use and which maintains sterility from one tube to the next.

SUMMARY OF THE INVENTION

A tube holding a sample of blood and having an end provided with a pierceable closure is partially evacuated of gas by an apparatus that has according to the invention a stationary guide defining an axis inclined at an angle to the horizontal. A needle fixed in the guide projects axially downward therein. A slide in the guide forms a downwardly inclined and open seat centered on the axis and adapted to receive the end of the tube. The slide is movable in the guide between an outer position with the seat spaced past an end of the needle and an inner use position with the needle projecting into the seat so that in the use position the needle projects through the closure of the tube fitted to the seat. The slide is urged axially downward in the guide, and a pump is provided for aspirating air through the needle.

Thus with this system the tube is never laid perfectly horizontal as in the above-described device, so that the blood in the tube is not in contact with the closure during the evacuating operation. Instead the tube is held at an angle by the evacuating apparatus so that when the needle pierces its closure, this needle will be out of contact with any fluid therein and will be able to withdraw gas from the tube until the desired subatmospheric pressure is established therein.

In accordance with the invention a spring is braced between the guide and the slide and constitutes the biasing means urging the slide downward. Furthermore according to the invention the tube is of such a length that, when fitted to the seat in the use position, it tube projects substantially from the slide.

Thus the device is simple to operate. All the user needs to do is push the partially filled tube upward into the slide until its closure end fits in the seat. A further push moves the tube and slide up and pierces the needle through the closure into the air space in the tube above the liquid therein. Normally this movement of the slide trips a switch that starts the evacuating pump that operates until the desired subatmospheric pressure is established in the tube.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
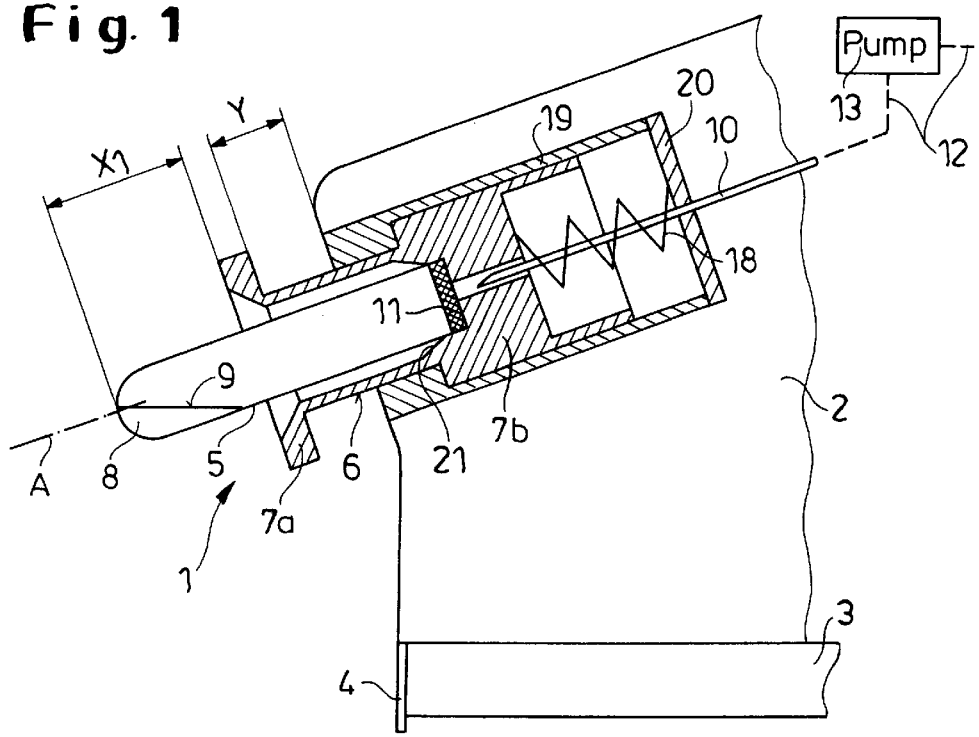
FIG. 1 is a partly diagrammatic vertical section through the apparatus according to the invention in a starting position.
Figure 2:
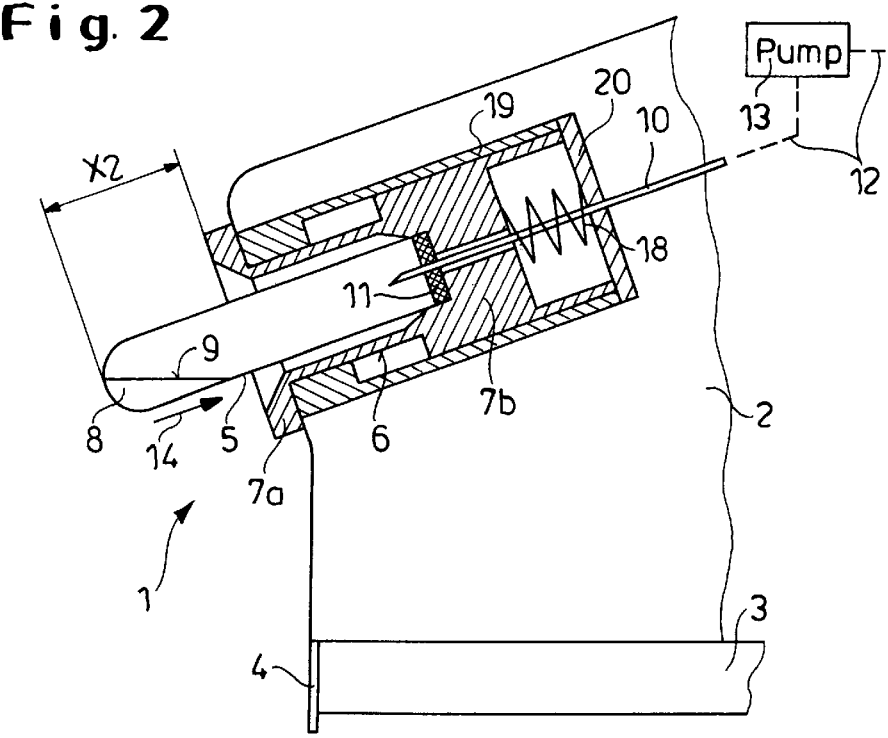
FIG. 2 is a view like FIG. 1 showing the apparatus in a use position.

As seen in FIGS. 1 and 2, an apparatus 1 serves for forming a partial vacuum in a blood tube 5 holding a pool 8 of blood having a surface 9. A pierceable membrane or plug 11 forms a closure at a mouth of the tube 5. The apparatus 1 has a base 3 adapted to sit on a horizontal surface and having an edge lip 4 so that it can be braced against an edge of the surface, for instance a lab table.

The base 3 carries a support 2 in turn carrying a normally stationary cylindrical guide 19 centered on an axis A inclined at an acute angle (here around 40°) to the horizontal and holding a slide 6 having an outer part 7a forming a seat 21 centered on the axis A and adapted to receive the tube 5 and an inner part 7b slidable axially in the guide 19. A spring 18 braced against an end plate 20 of the guide 19 urges the slide 6 axially downward. A needle 10 fixed in the end plate 20 is connected via a conduit 12 to a pump 13 that is set to withdraw air through the needle 10 until a predetermined subatmospheric pressure is reached.

In use as shown in FIG. 1 the tube 5 is inserted with its membrane 11 up into the seat 21 such that about one third of the tube 5 is exposed over a distance $X_1$ outside the slide 6. Then the user pushes the tube 5 and slide 6 axially upward in direction 14 through a distance Y so that as shown in FIG. 2 the needle 10 pierces the closure 11 and enters the upper part of the tube 5. Since the axis A is inclined, the needle 10 will be well above the surface 9 of the blood pool 8, even if the tube 5 is filled more than half. Once the needle 10 is through the closure 11, an unillustrated automatic switch turns on the pump 13 to suck air out of the tube 5 until the desired partial vacuum is created therein. In this use position the tube 5 extends from the slide 6 by a distance $X_2$ equal to $X_1$, and an outwardly projecting rim of the slide 6 buts solidly against an end of the guide 19.

Figure 3:
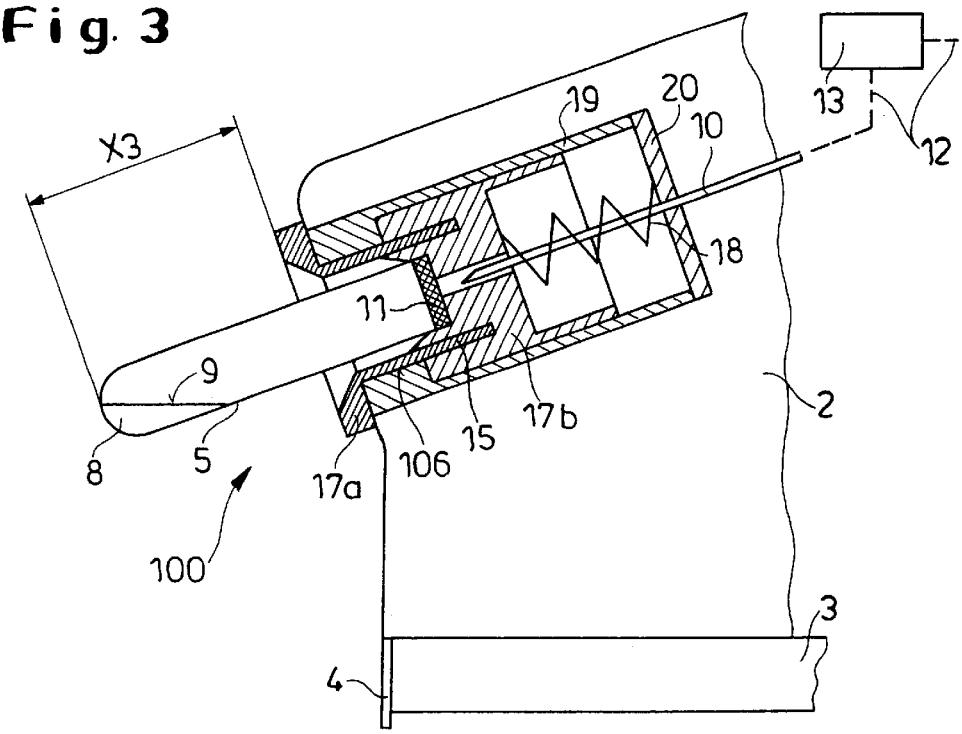
FIGS. 3 and 4 are views like FIGS. 1 and 2, respectively, of an alternative apparatus in accordance with the invention.
Figure 4:
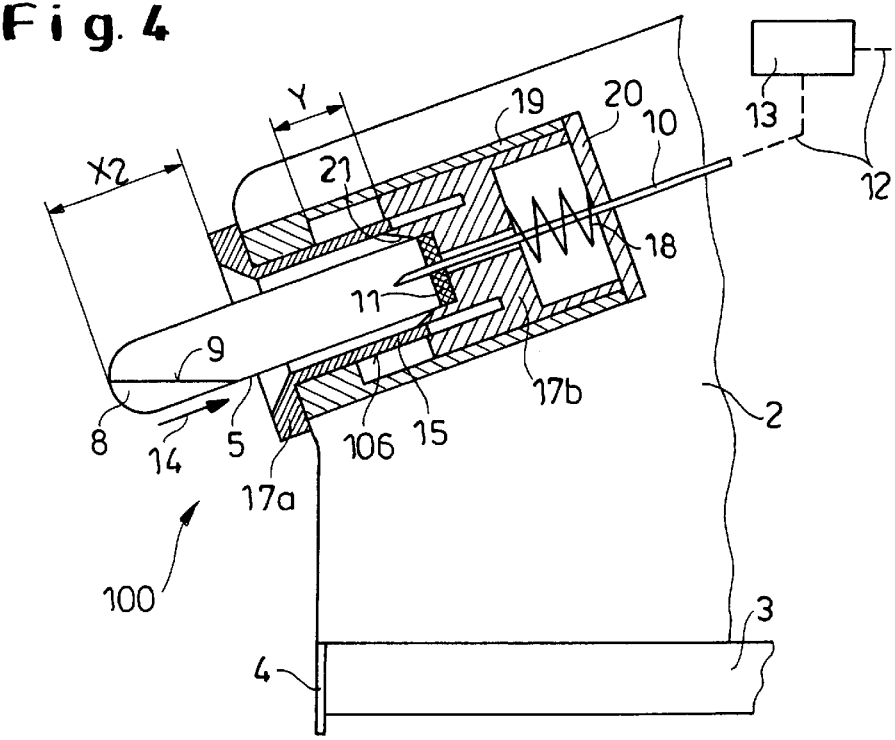

The apparatus 100 of FIGS. 3 and 4 is similar to that of FIGS. 1 and 2, identical reference numerals being used for functionally identical structure. Here there is a two-part slide 106 having an outer part 17a and an inner part 17b forming the seat 21 and braced against the spring 18. The outer part 17a has a sleeve 15 slidable axially through the distance Y in a complementary groove of the inner part 17b and is fixed to the guide 19 so as effectively to form a part of it.

Thus with this system to start with the tube 5 projects a distance $X_3$ substantially greater than the distance $X_1$ from the device. As the movable slide part 17b moves in, the distance $X_3$ drops to the smaller distance $X_2$. In any case enough of the tube 5 is left sticking out of the device that the user can hold it firmly, but is in no danger of contact with the blood inside the tube 5.

What is claimed is:

1. In combination with a tube holding a sample of blood and having an end provided with a pierceable closure, an apparatus for withdrawing gas from the tube comprising:

a stationary guide defining an axis inclined at an angle to the horizontal;

a needle fixed in the guide and projecting axially downward therein;

a slide in the guide forming a downwardly inclined and open seat centered on the axis and adapted to receive the end of the tube, the slide being movable in the guide between an outer position with the seat spaced past an end of the needle and an inner use position with the needle projecting into the seat, whereby in the use position the needle projects through the closure of the tube fitted to the seat;

biasing means for urging the slide axially downward in the guide; and means for aspirating air through the needle.

2. The apparatus defined in claim 1 wherein the biasing means is a spring braced between the guide and the slide.

3. The apparatus defined in claim 1 wherein the tube is of such a length that, when fitted to the seat in the use position, the tube projects substantially from the slide.

* * * * *